(12) United States Patent
Chen

(10) Patent No.: US 7,364,883 B2
(45) Date of Patent: Apr. 29, 2008

(54) PROCESS FOR PRODUCING POLY-UNSATURATED FATTY ACIDS BY OLEAGINOUS YEASTS

(75) Inventor: Tzu-Chih Chen, Taipei (TW)

(73) Assignee: Yeastern BioTech Co., Ltd., Taipei (TW)

( * ) Notice: Subject to any disclaimer, the term of this patent is extended or adjusted under 35 U.S.C. 154(b) by 0 days.

(21) Appl. No.: 11/123,115

(22) Filed: May 6, 2005

(65) Prior Publication Data

US 2005/0266537 A1 Dec. 1, 2005

Related U.S. Application Data

(60) Provisional application No. 60/568,692, filed on May 7, 2004.

(51) Int. Cl.
| | |
|---|---|
| C12N 1/16 | (2006.01) |
| C12N 1/13 | (2006.01) |
| C12N 1/19 | (2006.01) |
| C12N 1/18 | (2006.01) |
| C12N 9/10 | (2006.01) |
| C12P 21/06 | (2006.01) |
| C07H 21/04 | (2006.01) |
| C12Q 1/68 | (2006.01) |
| C12N 15/70 | (2006.01) |

(52) U.S. Cl. ............... 435/134; 435/252.3; 435/257.2; 435/254.11; 435/254.2; 435/6; 435/69.1; 435/190; 435/320.1; 536/23.2

(58) Field of Classification Search ............... 435/134, 435/6, 190, 254.2, 483; 536/23.2
See application file for complete search history.

(56) References Cited

U.S. PATENT DOCUMENTS

| | | | | |
|---|---|---|---|---|
| 5,968,809 | A * | 10/1999 | Knutzon et al. | ......... 435/254.2 |
| 6,136,574 | A | 10/2000 | Knutzon et al. | |
| 2003/0157144 | A1 | 8/2003 | Mukerji et al. | |
| 2004/0253621 | A1 | 12/2004 | Picataggio et al. | |
| 2005/0132442 | A1* | 6/2005 | Yadav et al. | ........... 800/281 |

FOREIGN PATENT DOCUMENTS

| | | |
|---|---|---|
| EP | 0 550 162 A1 | 7/1993 |
| EP | 0 561 569 A2 | 9/1993 |
| EP | 0 644 263 A2 | 3/1995 |
| EP | 0 736 598 A1 | 10/1996 |
| WO | WO-91/13972 A1 | 9/1991 |
| WO | WO-93/11245 A1 | 6/1993 |
| WO | WO-94/11516 A1 | 5/1994 |
| WO | WO-96/13591 A2 | 5/1996 |
| WO | WO-96/21022 A2 | 7/1996 |
| WO | WO-00/12720 A2 | 3/2000 |
| WO | WO 2004/101753 A2 * | 11/2004 |

OTHER PUBLICATIONS

Knutzon, D.S. et al.; Journal of Biological Chemistry, vol. 273, No. 45, pp. 29360-29366 (1998), XP-002106760.
Domergue, F. et al.; The Journal of Biological Chemistry, vol. 278, No. 37., pp. 35115-35126 (2003); XP-002313880.
Kajikawa, M. et al.; Plant Cell Physiology, vol. 47, No. 1, pp. 64-73 (2006), XP-002429337.
Aggelis, George et al., Biotechnology Letters, vol. 21, pp. 747-749 (1999); XP-002429336.
Papanikolaou, S. et al.; Bioresource Technology, vol. 82, pp. 43-49 (2002); XP-002429335.
Matsuo, N. et al.; Prostaglandins, Leukotrienes and Essential Fatty Acids; vol. 55, No. 4, pp. 223-229 (1996); XP-000882314.
Sakuradani, E. et al.; Eur. J. Biochem., 261, pp. 812-820 (1999); XP-000906848.

* cited by examiner

Primary Examiner—Rebecca Prouty
Assistant Examiner—Iqbal Chowdhury
(74) Attorney, Agent, or Firm—Birch, Stewart, Kolasch & Birch, LLP

(57) ABSTRACT

The present invention is directed to a process of producing novel fatty acids in oleaginous yeast by producing oleaginous yeast by introducing into the yeast genes coding for enzymes selected from the group consisting of D5-desaturase, D6-desaturase, D12-desaturase, D15-desaturase and elongase; and culturing the yeast in the medium containing high levels of carbon sources. The present invention is further directed to a residue or fatty acid that is obtained from pressing the oleaginous yeast produced by the process of the invention.

5 Claims, 9 Drawing Sheets

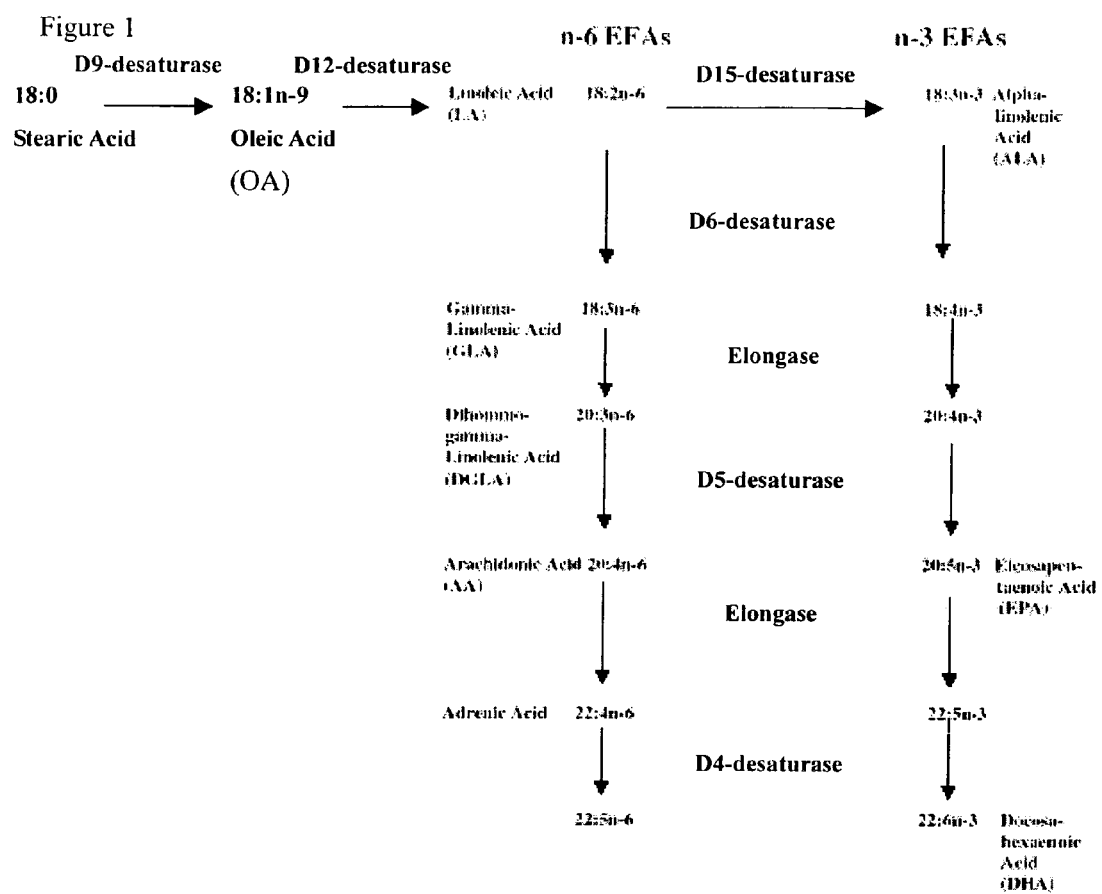

Figure 2A

```
  1  ATGGCTGCTG CTCCCAGTGT GAGGACGTTT ACTCGGGCCG
     AGGTTTTGAA
 51  TGCCGAGGCT CTGAATGAGG GCAAGAAGGA TGCCGAGGCA
     CCCTTCTTGA
101  TGATCATCGA CAACAAGGTG TACGATGTCC GCGAGTTCGT
     CCCTGATCAT
151  CCCGGTGGAA GTGTGATTCT CACGCACGTT GGCAAGGACG
     GCACTGACGT
201  CTTTGACACT TTTCACCCCG AGGCTGCTTG GGAGACTCTT
     GCCAACTTTT
251  ACGTTGGTGA TATTGACGAG AGCGACCGCG ATATCAAGAA
     TGATGACTTT
301  GCGGCCGAGG TCCGCAAGCT GCGTACCTTG TTCCAGTCTC
     TTGGTTACTA
351  CGATTCTTCC AAGGCATACT ACGCCTTCAA GGTCTCGTTC
     AACCTCTGCA
401  TCTGGGGTTT GTCGACGGTC ATTGTGGCCA AGTGGGGCCA
     GACCTCGACC
451  CTCGCCAACG TGCTCTCGGC TGCGCTTTTG GGTCTGTTCT
     GGCAGCAGTG
501  CGGATGGTTG GCTCACGACT TTTTGCATCA CCAGGTCTTC
     CAGGACCGTT
551  TCTGGGGTGA TCTTTTCGGC GCCTTCTTGG GAGGTGTCTG
     CCAGGGCTTC
601  TCGTCCTCGT GGTGGAAGGA CAAGCACAAC ACTCACCACG
     CCGCCCCCAA
651  CGTCCACGGC GAGGATCCCG ACATTGACAC CCACCCTCTG
     TTGACCTGGA
701  GTGAGCATGC GTTGGAGATG TTCTCGGATG TCCCAGATGA
     GGAGCTGACC
751  CGCATGTGGT CGCGTTTCAT GGTCCTGAAC CAGACCTGGT
     TTTACTTCCC
801  CATTCTCTCG TTTGCCCGTC TCTCCTGGTG CCTCCAGTCC
     ATTCTCTTTG
851  TGCTGCCTAA CGGTCAGGCC CACAAGCCCT CGGGCGCGCG
     TGTGCCCATC
```

Figure 2B

```
 901   TCGTTGGTCG  AGCAGCTGTC  GCTTGCGATG  CACTGGACCT
       GGTACCTCGC
 951   CACCATGTTC  CTGTTCATCA  AGGATCCCGT  CAACATGCTG
       GTGTACTTTT
1001   TGGTGTCGCA  GGCGGTGTGC  GGAAACTTGT  TGGCGATCGT
       GTTCTCGCTC
1051   AACCACAACG  GTATGCCTGT  GATCTCGAAG  GAGGAGGCGG
       TCGATATGGA
1101   TTTCTTCACG  AAGCAGATCA  TCACGGGTCG  TGATGTCCAC
       CCGGGTCTAT
1151   TTGCCAACTG  GTTCACGGGT  GGATTGAACT  ATCAGATCGA
       GCACCACTTG
1201   TTCCCTTCGA  TGCCTCGCCA  CAACTTTTCA  AGATCCAGC
       CTGCTGTCGA
1251   GACCCTGTGC  AAAAAGTACA  ATGTCCGATA  CCACACCACC
       GGTATGATCG
1301   AGGGAACTGC  AGAGGTCTTT  AGCCGTCTGA  ACGAGGTCTC
       CAAGGCTGCC
1351   TCCAAGATGG  GTAAGGCGCA  GTAA  (SEQ ID NO:1)
```

Figure 3A

```
  1 ATGGCACCTC CCAACACTAT CGATGCCGGT TTGACCCAGC
    GTCATATCAG
 51 CACCTCGGCC CCAAACTCGG CCAAGCCTGC CTTCGAGCGC
    AACTACCAGC
101 TCCCCGAGTT CACCATCAAG GAGATCCGAG AGTGCATCCC
    TGCCCACTGC
151 TTTGAGCGCT CCGGTCTCCG TGGTCTCTGC CACGTTGCCA
    TCGATCTGAC
201 TTGGGCGTCG CTCTTGTTCC TGGCTGCGAC CCAGATCGAC
    AAGTTTGAGA
251 ATCCCTTGAT CCGCTATTTG GCCTGGCCTG TTTACTGGAT
    CATGCAGGGT
301 ATTGTCTGCA CCGGTGTCTG GGTGCTGGCT CACGAGTGTG
    GTCATCAGTC
351 CTTCTCGACC TCCAAGACCC TCAACAACAC AGTTGGTTGG
    ATCTTGCACT
401 CGATGCTCTT GGTCCCCTAC CACTCCTGGA GAATCTCGCA
    CTCGAAGCAC
451 CACAAGGCCA CTGGCCATAT GACCAAGGAC CAGGTCTTTG
    TGCCCAAGAC
501 CCGCTCCCAG GTTGGCTTGC CTCCCAAGGA GAACGCTGCT
    GCTGCCGTTC
551 AGGAGGAGGA CATGTCCGTG CACCTGGATG AGGAGGCTCC
    CATTGTGACT
601 TTGTTCTGGA TGGTGATCCA GTTCTTGTTC GGATGGCCCG
    CGTACCTGAT
651 TATGAACGCC TCTGGCCAAG ACTACGGCCG CTGGACCTCG
    CACTTCCACA
701 CGTACTCGCC CATCTTTGAG CCCCGCAACT TTTTCGACAT
    TATTATCTCG
751 GACCTCGGTG TGTTGGCTGC CCTCGGTGCC CTGATCTATG
    CCTCCATGCA
801 GTTGTCGCTC TTGACCGTCA CCAAGTACTA TATTGTCCCC
    TACCTCTTTG
851 TCAACTTTTG GTTGGTCCTG ATCACCTTCT TGCAGCACAC
    CGATCCCAAG
```

Figure 3B

```
 901  CTGCCCCATT ACCGCGAGGG TGCCTGGAAT TTCCAGCGTG
      GAGCTCTTTG
 951  CACCGTTGAC CGCTCGTTTG GCAAGTTCTT GGACCATATG
      TTCCACGGCA
1001  TTGTCCACAC CCATGTGGCC CATCACTTGT TCTCGCAAAT
      GCCGTTCTAC
1051  CATGCTGAGG AAGCTACCTA TCATCTCAAG AAACTGCTGG
      GAGAGTACTA
1101  TGTGTACGAC CCATCCCCGA TCGTCGTTGC GGTCTGGAGG
      TCGTTCCGTG
1151  AGTGCCGATT CGTGGAGGAT CAGGGAGACG TGGTCTTTTT
      CAAGAAGTAA  (SEQ ID NO:2)
```

Figure 4

Delta 6 primer sets of gene synthesis

D6F1:5'- atggctgctgctcccagtgtgaggacgtttactcgggccgaggttttgaatgccgaggct-3' (SEQ ID NO:3)
D6F2:5'- tgccgaggcacccttcttgatgatcatcgacaacaaggtgtacgatgtccgcgagttcgt-3' (SEQ ID NO:4)
D6F3:5'- gtgtgattctcacgcacgttggcaaggacggcactgacgtctttgacactttcaccccg-3' (SEQ ID NO:5)
D6F4:5'- gccaacttttacgttggtgatattgacgagagcgaccgcgatatcaagaatgatgacttt-3' (SEQ ID NO:6)
D6F5:5'- gcgtaccttgttccagtctcttggttactacgattcttccaaggcatactacgccttcaa-3' (SEQ ID NO:7)
D6F6:5'- tctggggtttgtcgacggtcattgtggccaagtggggccagacctcgaccctcgccaacg-3' (SEQ ID NO:8)
D6F7:5'- ggtctgttctggcagcagtgcggatggttggctcacgacttttgcatcaccaggtcttc-3' (SEQ ID NO:9)
D6F8:5'- tcttttcggcgccttcttgggaggtgtctgccagggcttctcgtcctcgtggtggaagga-3' (SEQ ID NO:10)
D6F9:5'- ccgcccccaacgtccacggcgaggatcccgacattgacacccaccctctgttgacctgga-3' (SEQ ID NO:11)
D6F10:5'- ttctcggatgtcccagatgaggagctgacccgcatgtggtcgcgtttcatggtcctgaac-3' (SEQ ID NO:12)
D6F11:5'- cattctctcgtttgcccgtctctcctggtgcctccagtccattctctttgtgctgcctaa-3' (SEQ ID NO:13)
D6F12:5'- cgggcgcgcgtgtgcccatctcgttggtcgagcagctgtcgcttgcgatgcactggacct-3' (SEQ ID NO:14)
D6F13:5'- ctgttcatcaaggatcccgtcaacatgctggtgtacttttggtgtcgcaggcggtgtgc-3' (SEQ ID NO:15)
D6F14:5'- gttctcgctcaaccacaacggtatgcctgtgatctcgaaggaggaggcggtcgatatgga-3' (SEQ ID NO:16)
D6F15:5'- tcacgggtcgtgatgtccaccccgggtctatttgccaactggttcacgggtggattgaact-3' (SEQ ID NO:17)
D6F16:5'- ttcccttcgatgcctcgccacaacttttcaaagatccagcctgctgtcgagaccctgtgc-3' (SEQ ID NO:18)
D6F17:5'- ccacaccaccggtatgatcgagggaactgcagaggtctttagccgtctgaacgaggtctc-3' (SEQ ID NO:19)

D6R1:5'- tcaagaagggtgcctcggcatccttcttgccctcattcagagcctcggcattcaaaacct-3' (SEQ ID NO:20)
D6R2:5'- aacgtgcgtgagaatcacacttccaccgggatgatcagggacgaactcgcggacatcgta-3' (SEQ ID NO:21)
D6R3:5'- tcaccaacgtaaaagttggcaagagtctcccaagcagcctcggggtgaaaagtgtcaaag-3' (SEQ ID NO:22)
D6R4:5'- gagactggaacaaggtacgcagcttgcggacctcggccgcaaagtcatcattcttgatat-3' (SEQ ID NO:23)
D6R5:5'- gaccgtcgacaaaccccagatgcagaggttgaacgagaccttgaaggcgtagtatgcctt-3' (SEQ ID NO:24)
D6R6:5'- cactgctgccagaacagacccaaaagcgcagccgagagcacgttggcgagggtcgaggtc-3' (SEQ ID NO:25)
D6R7:5'- ccaagaaggcgccgaaaagatcaccccagaaacggtcctggaagacctggtgatgcaaaa-3' (SEQ ID NO:26)
D6R8:5'- gccgtggacgttgggggcggcgtggtgagtgttgtgcttgtccttccaccacgaggacga-3' (SEQ ID NO:27)
D6R9:5'- tcatctgggacatccgagaacatctccaacgcatgctcactccaggtcaacagagggtgg-3' (SEQ ID NO:28)
D6R10:5'- gacgggcaaacgagagaatggggaagtaaaaccaggtctggttcaggaccatgaaacgcg-3' (SEQ ID NO:29)
D6R11:5'- gatgggcacacgcgcgccccgagggcttgtgggcctgaccgttaggcagcacaaagagaat-3' (SEQ ID NO:30)
D6R12:5'- acgggatccttgatgaacaggaacatggtggcgaggtaccaggtccagtgcatcgcaagc-3' (SEQ ID NO:31)
D6R13:5'- cgttgtggttgagcgagaacacgatcgccaacaagtttccgcacaccgcctgcgacacca-3' (SEQ ID NO:32)
D6R14:5'- gtggacatcacgacccgtgatgatctgcttcgtgaagaaatccatatcgaccgcctcctc-3' (SEQ ID NO:33)
D6R15:5'- tggcgaggcatcgaagggaacaagtggtgctcgatctgatagttcaatccaccgtgaac-3' (SEQ ID NO:34)
D6R16:5'- cgatcataccggtggtgtggtatcggacattgtactttttgcacagggtctcgacagcag-3' (SEQ ID NO:35)
D6R17:5'- ttactgcgccttacccatcttggaggcagccttggagacctcgttcagacggct-3' (SEQ ID NO:36)

Figure 5

Delta 12 primer sets of gene synthesis

D12F1:5'- atggcacctcccaacactatcgatgccggtttgacccagcgtcatatcagcacctcggcc-3' (SEQ ID NO:37)
D12F2:5'- cttcgagcgcaactaccagctccccgagttcaccatcaaggagatccgagagtgcatccc-3' (SEQ ID NO:38)
D12F3:5'- ccggtctccgtggtctctgccacgttgccatcgatctgacttgggcgtcgctcttgttcc-3' (SEQ ID NO:39)
D12F4:5'- aagtttgagaatcccttgatccgctatttggcctggcctgtttactggatcatgcagggt-3' (SEQ ID NO:40)
D12F5:5'- ggtgctggctcacgagtgtggtcatcagtccttctcgacctccaagaccctcaacaacac-3' (SEQ ID NO:41)
D12F6:5'- cgatgctcttggtcccctaccactcctggagaatctcgcactcgaagcaccacaaggcca-3' (SEQ ID NO:42)
D12F7:5'- caggtctttgtgcccaagacccgctcccaggttggcttgcctcccaaggagaacgctgct-3' (SEQ ID NO:43)
D12F8:5'- catgtccgtgcacctggatgaggaggctcccattgtgactttgttctggatggtgatcca-3' (SEQ ID NO:44)
D12F9:5'- cgtacctgattatgaacgcctctggccaagactacggccgctggacctcgcacttccaca-3' (SEQ ID NO:45)
D12F10:5'- ccccgcaacttttcgacattattatctcggacctcggtgtgttggctgccctcggtgcc-3' (SEQ ID NO:46)
D12F11:5'- gttgtcgctcttgaccgtcaccaagtactatattgtccctacctctttgtcaacttttg-3' (SEQ ID NO:47)
D12F12:5'- tgcagcacaccgatcccaagctgccccattaccgcgagggtgcctggaatttccagcgtg-3' (SEQ ID NO:48)
D12F13:5'- cgctcgtttggcaagttcttggaccatatgttccacggcattgtccacacccatgtggcc-3' (SEQ ID NO:49)
D12F14:5'- gccgttctaccatgctgaggaagctacctatcatctcaagaaaactgctgggagagtacta-3' (SEQ ID NO:50)
D12F15:5'- tcgtcgttgcggtctggaggtcgttccgtgagtgccgattcgtggaggatcagggagacg-3' (SEQ ID NO:51)

D12R1:5'- gctggtagttgcgctcgaaggcaggcttggccgagtttggggccgaggtgctgatatgac-3' (SEQ ID NO:52)
D12R2:5'- gcagagaccacggagaccggagcgctcaaagcagtgggcagggatgcactctcggatctc-3' (SEQ ID NO:53)
D12R3:5'- atcaagggattctcaaacttgtcgatctgggtcgcagccaggaacaagagcgacgcccaa-3' (SEQ ID NO:54)
D12R4:5'- cacactcgtgagccagcacccagacaccggtgcagacaataccctgcatgatccagtaaa-3' (SEQ ID NO:55)
D12R5:5'- gtaggggaccaagagcatcgagtgcaagatccaaccaactgtgttgttgagggtcttgga-3' (SEQ ID NO:56)
D12R6:5'- gtcttgggcacaaagacctggtccttggtcatatggccagtggccttgtggtgcttcgag-3' (SEQ ID NO:57)
D12R7:5'- catccaggtgcacggacatgtcctcctcctgaacggcagcagcagcgttctccttgggag-3' (SEQ ID NO:58)
D12R8:5'- ggcgttcataatcaggtacgcgggccatccgaacaagaactggatcaccatccagaacaa-3' (SEQ ID NO:59)
D12R9:5'- atgtcgaaaaagttgcggggctcaaagatgggcgagtacgtgtggaagtgcgaggtcca-3' (SEQ ID NO:60)
D12R10:5'- tgacggtcaagagcgacaactgcatggaggcatagatcagggcaccgagggcagccaaca-3' (SEQ ID NO:61)
D12R11:5'- cttgggatcggtgtgctgcaagaaggtgatcaggaccaaccaaaagttgacaaagaggta-3' (SEQ ID NO:62)
D12R12:5'- aagaacttgccaaacgagcggtcaacggtgcaaagagctccacgctggaaattccaggca-3' (SEQ ID NO:63)
D12R13:5'- cctcagcatggtagaacggcatttgcgagaacaagtgatgggccacatgggtgtggacaa-3' (SEQ ID NO:64)
D12R14:5'- cctccagaccgcaacgacgatcggggatgggtcgtacacatagtactctcccagcagttt-3' (SEQ ID NO:65)
D12R15:5'- ttacttcttgaaaaagaccacgtctccctgatcctccacg-3' (SEQ ID NO:66)

SEQUENCE LISTING

<160> NUMBER OF SEQ ID NOS: 70

<210> SEQ ID NO 1
<211> LENGTH: 1374
<212> TYPE: DNA
<213> ORGANISM: Mortierella alpina
<220> FEATURE:
<221> NAME/KEY: gene
<222> LOCATION: (1)..(1374)
<223> OTHER INFORMATION: cDNA sequence of D6-desaturase.

<400> SEQUENCE: 1

| | | | | | |
|---|---|---|---|---|---|
| atggctgctg | ctcccagtgt | gaggacgttt | actcgggccg | aggttttgaa tgccgaggct | 60 |
| ctgaatgagg | gcaagaagga | tgccgaggca | cccttcttga | tgatcatcga caacaaggtg | 120 |
| tacgatgtcc | gcgagttcgt | ccctgatcat | cccggtggaa | gtgtgattct cacgcacgtt | 180 |
| ggcaaggacg | gcactgacgt | ctttgacact | tttcaccccg | aggctgcttg ggagactctt | 240 |
| gccaactttt | acgttggtga | tattgacgag | agcgaccgcg | atatcaagaa tgatgacttt | 300 |
| gcggccgagt | ccgcaagct | gcgtaccttg | ttccagtctc | ttggttacta cgattcttcc | 360 |
| aaggcatact | acgccttcaa | ggtctcgttc | aacctctgca | tctggggttt gtcgacggtc | 420 |
| attgtggcca | gtggggcca | gacctcgacc | ctcgccaacg | tgctctcggc tgcgcttttg | 480 |
| ggtctgttct | ggcagcagtg | cggatggttg | gctcacgact | ttttgcatca ccaggtcttc | 540 |
| caggaccgtt | tctggggtga | tcttttcggc | gccttcttgg | gaggtgtctg ccagggcttc | 600 |
| tcgtcctcgt | ggtggaagga | caagcacaac | actcaccacg | ccgcccccaa cgtccacggc | 660 |
| gaggatcccg | acattgacac | ccaccctctg | ttgacctgga | gtgagcatgc gttggagatg | 720 |
| ttctcggatg | tcccagatga | ggagctgacc | cgcatgtggt | cgcgtttcat ggtcctgaac | 780 |
| cagacctggt | tttacttccc | cattctctcg | tttgcccgtc | tctcctggtg cctccagtcc | 840 |
| attctctttg | tgctgcctaa | cggtcaggcc | acaagccct | cgggcgcgcg tgtgcccatc | 900 |
| tcgttggtcg | agcagctgtc | gcttgcgatg | cactggacct | ggtacctcgc caccatgttc | 960 |
| ctgttcatca | aggatcccgt | caacatgctg | gtgtactttt | tggtgtcgca ggcggtgtgc | 1020 |
| ggaaacttgt | tggcgatcgt | gttctcgctc | aaccacaacg | gtatgcctgt gatctcgaag | 1080 |
| gaggaggcgg | tcgatatgga | tttcttcacg | aagcagatca | tcacgggtcg tgatgtccac | 1140 |
| ccgggtctat | tgccaactg | gttcacgggt | ggattgaact | atcagatcga gcaccacttg | 1200 |
| ttcccttcga | tgcctcgcca | caacttttca | agatccagc | tgctgtcga gaccctgtgc | 1260 |
| aaaaagtaca | atgtccgata | ccacaccacc | ggtatgatcg | agggaactgc agaggtcttt | 1320 |
| agccgtctga | acgaggtctc | caaggctgcc | tccaagatgg | gtaaggcgca gtaa | 1374 |

<210> SEQ ID NO 2
<211> LENGTH: 1200
<212> TYPE: DNA
<213> ORGANISM: Mortierella alpina
<220> FEATURE:
<221> NAME/KEY: gene
<222> LOCATION: (1)..(1200)
<223> OTHER INFORMATION: cDNA sequence of D12-desaturase

<400> SEQUENCE: 2

| | | | | | |
|---|---|---|---|---|---|
| atggcacctc | ccaacactat | cgatgccggt | ttgacccagc | gtcatatcag cacctcggcc | 60 |
| ccaaactcgg | ccaagcctgc | cttcgagcgc | aactaccagc | tccccgagtt caccatcaag | 120 |
| gagatccgag | agtgcatccc | tgcccactgc | tttgagcgct | ccggtctccg tggtctctgc | 180 |

```
cacgttgcca tcgatctgac ttgggcgtcg ctcttgttcc tggctgcgac ccagatcgac      240
aagtttgaga atcccttgat ccgctatttg gcctggcctg tttactggat catgcagggt      300
attgtctgca ccggtgtctg ggtgctggct cacgagtgtg gtcatcagtc cttctcgacc      360
tccaagaccc tcaacaacac agttggttgg atcttgcact cgatgctctt ggtcccctac      420
cactcctgga gaatctcgca ctcgaagcac acaaggcca ctggccatat gaccaaggac       480
caggtctttg tgcccaagac ccgctcccag gttggcttgc ctcccaagga gaacgctgct      540
gctgccgttc aggaggagga catgtccgtg cacctggatg aggaggctcc cattgtgact      600
ttgttctgga tggtgatcca gttcttgttc ggatggcccg cgtacctgat tatgaacgcc      660
tctggccaag actacggccg ctggacctcg cacttccaca cgtactcgcc catctttgag      720
ccccgcaact ttttcgacat tattatctcg gacctcggtg tgttggctgc cctcggtgcc      780
ctgatctatg cctccatgca gttgtcgctc ttgaccgtca ccaagtacta tattgtcccc      840
tacctctttg tcaactttg gttggtcctg atcaccttct tgcagcacac cgatcccaag      900
ctgccccatt accgcgaggg tgcctggaat ttccagcgtg agctctttg caccgttgac      960 cgctcgtttg gcaagttctt ggaccatatg ttccacggca ttgtccacac ccatgtggcc     1020
catcacttgt tctcgcaaat gccgttctac catgctgagg aagctaccta tcatctcaag     1080
aaactgctgg gagagtacta tgtgtacgac ccatccccga tcgtcgttgc ggtctggagg     1140
tcgttccgtg agtgccgatt cgtggaggat cagggagacg tggtcttttt caagaagtaa     1200
```

<210> SEQ ID NO 3
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 3

```
atggctgctg ctcccagtgt gaggacgttt actcgggccg aggttttgaa tgccgaggct      60
```

<210> SEQ ID NO 4
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 4

```
tgccgaggca cccttcttga tgatcatcga caacaaggtg tacgatgtcc gcgagttcgt      60
```

<210> SEQ ID NO 5
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 5

```
gtgtgattct cacgcacgtt ggcaaggacg gcactgacgt ctttgacact tttcaccccg      60
```

<210> SEQ ID NO 6

```
<210> SEQ ID NO 6
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 6
gccaactttt acgttggtga tattgacgag agcgaccgcg atatcaagaa tgatgacttt    60

<210> SEQ ID NO 7
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 7
gcgtaccttg ttccagtctc ttggttacta cgattcttcc aaggcatact acgccttcaa    60

<210> SEQ ID NO 8
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 8
tctggggttt gtcgacggtc attgtggcca agtggggcca gacctcgacc ctcgccaacg    60

<210> SEQ ID NO 9
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 9
ggtctgttct ggcagcagtg cggatggttg gctcacgact ttttgcatca ccaggtcttc    60

<210> SEQ ID NO 10
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 10
tcttttcggc gccttcttgg gaggtgtctg ccagggcttc tcgtcctcgt ggtggaagga    60

<210> SEQ ID NO 11
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 11
```
ccgcccccaa cgtccacggc gaggatcccg acattgacac ccaccctctg ttgacctgga    60

<210> SEQ ID NO 12
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 12
ttctcggatg tcccagatga ggagctgacc cgcatgtggt cgcgtttcat ggtcctgaac    60

<210> SEQ ID NO 13
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 13
cattctctcg tttgcccgtc tctcctggtg cctccagtcc attctctttg tgctgcctaa    60

<210> SEQ ID NO 14
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 14
cgggcgcgcg tgtgcccatc tcgttggtcg agcagctgtc gcttgcgatg cactggacct    60

<210> SEQ ID NO 15
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 15
ctgttcatca aggatcccgt caacatgctg gtgtactttt tggtgtcgca ggcggtgtgc    60

<210> SEQ ID NO 16
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 16
gttctcgctc aaccacaacg gtatgcctgt gatctcgaag gaggaggcgg tcgatatgga    60

<210> SEQ ID NO 17
<211> LENGTH: 60
<212> TYPE: DNA
<213> ORGANISM: Mortierella alpine
<220> FEATURE:

```
<221> NAME/KEY: primer
<222> LOCATION: (1)..(60)
<223> OTHER INFORMATION: forward primer of D6-desaturase gene

<400> SEQUENCE: 17
tcacgggtcg tgatgtccac ccgggtctat ttgccaactg gttcacgggt ggattgaact      60

<210> SEQ ID NO 18
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 18
ttcccttcga tgcctcgcca caacttttca aagatccagc ctgctgtcga gaccctgtgc      60

<210> SEQ ID NO 19
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D6-desaturase gene

<400> SEQUENCE: 19
ccacaccacc ggtatgatcg agggaactgc agaggtcttt agccgtctga acgaggtctc      60

<210> SEQ ID NO 20
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 20
tcaagaaggg tgcctcggca tccttcttgc cctcattcag agcctcggca ttcaaaacct      60

<210> SEQ ID NO 21
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 21
aacgtgcgtg agaatcacac ttccaccggg atgatcaggg acgaactcgc ggacatcgta      60

<210> SEQ ID NO 22
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 22
tcaccaacgt aaaagttggc aagagtctcc caagcagcct cggggtgaaa agtgtcaaag      60
```

```
<210> SEQ ID NO 23
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 23
gagactggaa caaggtacgc agcttgcgga cctcggccgc aaagtcatca ttcttgatat    60

<210> SEQ ID NO 24
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 24
gaccgtcgac aaacccaga tgcagaggtt gaacgagacc ttgaaggcgt agtatgcctt    60

<210> SEQ ID NO 25
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 25
cactgctgcc agaacagacc caaaagcgca gccgagagca cgttggcgag ggtcgaggtc    60

<210> SEQ ID NO 26
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 26
ccaagaaggc gccgaaaaga tcaccccaga acggtcctg gaagacctgg tgatgcaaaa    60

<210> SEQ ID NO 27
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 27
gccgtggacg ttgggggcgg cgtggtgagt gttgtgcttg tccttccacc acgaggacga    60

<210> SEQ ID NO 28
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene
```

```
<400> SEQUENCE: 28
tcatctggga catccgagaa catctccaac gcatgctcac tccaggtcaa cagagggtgg    60

<210> SEQ ID NO 29
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 29
gacgggcaaa cgagagaatg gggaagtaaa accaggtctg gttcaggacc atgaaacgcg    60

<210> SEQ ID NO 30
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 30
gatgggcaca cgcgcgcccg agggcttgtg ggcctgaccg ttaggcagca caaagagaat    60

<210> SEQ ID NO 31
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 31
acgggatcct tgatgaacag gaacatggtg gcgaggtacc aggtccagtg catcgcaagc    60

<210> SEQ ID NO 32
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 32
cgttgtggtt gagcgagaac acgatcgcca acaagtttcc gcacaccgcc tgcgacacca    60

<210> SEQ ID NO 33
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 33
gtggacatca cgacccgtga tgatctgctt cgtgaagaaa tccatatcga ccgcctcctc    60

<210> SEQ ID NO 34
<211> LENGTH: 60
<212> TYPE: DNA
<213> ORGANISM: Mortierella alpine
```

```
<220> FEATURE:
<221> NAME/KEY: primer
<222> LOCATION: (1)..(60)
<223> OTHER INFORMATION: reverse primer of D6-desaturase gene

<400> SEQUENCE: 34
tggcgaggca tcgaagggaa caagtggtgc tcgatctgat agttcaatcc acccgtgaac    60

<210> SEQ ID NO 35
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D6-desaturase gene

<400> SEQUENCE: 35
cgatcatacc ggtggtgtgg tatcggacat tgtactttt gcacagggtc tcgacagcag     60

<210> SEQ ID NO 36
<211> LENGTH: 54
<212> TYPE: DNA
<213> ORGANISM: Mortierella alpine
<220> FEATURE:
<221> NAME/KEY: primer
<222> LOCATION: (1)..(54)
<223> OTHER INFORMATION: reverse primer of D6-desaturase gene

<400> SEQUENCE: 36
ttactgcgcc ttacccatct tggaggcagc cttggagacc tcgttcagac ggct           54

<210> SEQ ID NO 37
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 37
atggcacctc ccaacactat cgatgccggt ttgacccagc gtcatatcag cacctcggcc    60

<210> SEQ ID NO 38
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 38
cttcgagcgc aactaccagc tccccgagtt caccatcaag gagatccgag agtgcatccc    60

<210> SEQ ID NO 39
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 39
ccggtctccg tggtctctgc cacgttgcca tcgatctgac ttgggcgtcg ctcttgttcc    60
```

<210> SEQ ID NO 40
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 40
aagtttgaga atcccttgat ccgctatttg gcctggcctg tttactggat catgcagggt    60

<210> SEQ ID NO 41
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 41
ggtgctggct cacgagtgtg gtcatcagtc cttctcgacc tccaagaccc tcaacaacac    60

<210> SEQ ID NO 42
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 42
cgatgctctt ggtcccctac cactcctgga gaatctcgca ctcgaagcac cacaaggcca    60

<210> SEQ ID NO 43
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 43
caggtctttg tgcccaagac ccgctcccag gttggcttgc ctcccaagga gaacgctgct    60

<210> SEQ ID NO 44
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 44
catgtccgtg cacctggatg aggaggctcc cattgtgact ttgttctgga tggtgatcca    60

<210> SEQ ID NO 45
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

```
<400> SEQUENCE: 45
cgtacctgat tatgaacgcc tctggccaag actacggccg ctggacctcg cacttccaca      60

<210> SEQ ID NO 46
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 46
ccccgcaact ttttcgacat tattatctcg gacctcggtg tgttggctgc cctcggtgcc      60

<210> SEQ ID NO 47
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 47
gttgtcgctc ttgaccgtca ccaagtacta tattgtcccc tacctctttg tcaactttttg     60

<210> SEQ ID NO 48
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 48
tgcagcacac cgatcccaag ctgccccatt accgcgaggg tgcctggaat ttccagcgtg      60

<210> SEQ ID NO 49
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 49
cgctcgtttg gcaagttctt ggaccatatg ttccacggca ttgtccacac ccatgtggcc      60

<210> SEQ ID NO 50
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 50
gccgttctac catgctgagg aagctaccta tcatctcaag aaactgctgg gagagtacta      60

<210> SEQ ID NO 51
<211> LENGTH: 60
<212> TYPE: DNA
```

```
<213> ORGANISM: Mortierella alpine
<220> FEATURE:
<221> NAME/KEY: primer
<222> LOCATION: (1)..(60)
<223> OTHER INFORMATION: forward primer of D12-desaturase gene

<400> SEQUENCE: 51
tcgtcgttgc ggtctggagg tcgttccgtg agtgccgatt cgtggaggat cagggagacg    60

<210> SEQ ID NO 52
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 52
gctggtagtt gcgctcgaag gcaggcttgg ccgagtttgg ggccgaggtg ctgatatgac    60

<210> SEQ ID NO 53
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 53
gcagagacca cggagaccgg agcgctcaaa gcagtgggca gggatgcact ctcggatctc    60

<210> SEQ ID NO 54
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 54
atcaagggat tctcaaactt gtcgatctgg gtcgcagcca ggaacaagag cgacgcccaa    60

<210> SEQ ID NO 55
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 55
cacactcgtg agccagcacc cagacaccgg tgcagacaat accctgcatg atccagtaaa    60

<210> SEQ ID NO 56
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 56
gtaggggacc aagagcatcg agtgcaagat ccaaccaact gtgttgttga gggtcttgga    60
```

<210> SEQ ID NO 57
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 57
gtcttgggca caaagacctg gtccttggtc atatggccag tggccttgtg gtgcttcgag    60

<210> SEQ ID NO 58
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 58
catccaggtg cacggacatg tcctcctcct gaacggcagc agcagcgttc tccttgggag    60

<210> SEQ ID NO 59
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 59
ggcgttcata atcaggtacg cgggccatcc gaacaagaac tggatcacca tccagaacaa    60

<210> SEQ ID NO 60
<211> LENGTH: 59
<212> TYPE: DNA
<213> ORGANISM: Mortierella alpine
<220> FEATURE:
<221> NAME/KEY: primer
<222> LOCATION: (1)..(59)
<223> OTHER INFORMATION: reverse primer of D12-desaturase gene

<400> SEQUENCE: 60
atgtcgaaaa agttgcgggg ctcaaagatg ggcgagtacg tgtggaagtg cgaggtcca    59

<210> SEQ ID NO 61
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 61
tgacggtcaa gagcgacaac tgcatggagg catagatcag ggcaccgagg gcagccaaca    60

<210> SEQ ID NO 62
<211> LENGTH: 60
<212> TYPE: DNA
<213> ORGANISM: Mortierella alpine
<220> FEATURE:
<221> NAME/KEY: primer
<222> LOCATION: (1)..(60)

```
<223> OTHER INFORMATION: reverse primer of D12-desaturase gene

<400> SEQUENCE: 62
cttgggatcg gtgtgctgca agaaggtgat caggaccaac caaaagttga caaagaggta      60

<210> SEQ ID NO 63
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 63
aagaacttgc caaacgagcg gtcaacggtg caaagagctc cacgctggaa attccaggca      60

<210> SEQ ID NO 64
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 64
cctcagcatg gtagaacggc atttgcgaga acaagtgatg ggccacatgg gtgtggacaa      60

<210> SEQ ID NO 65
<211> LENGTH: 60
<212> TYPE: DNA
<213> ORGANISM: Mortierella alpine
<220> FEATURE:
<221> NAME/KEY: primer
<222> LOCATION: (1)..(60)
<223> OTHER INFORMATION: reverse primer of D12-desaturase gene

<400> SEQUENCE: 65
cctccagacc gcaacgacga tcggggatgg gtcgtacaca tagtactctc ccagcagttt      60

<210> SEQ ID NO 66
<211> LENGTH: 40
<212> TYPE: DNA
<213> ORGANISM: Mortierella alpine
<220> FEATURE:
<221> NAME/KEY: primer
<222> LOCATION: (1)..(40)
<223> OTHER INFORMATION: reverse primer of D12-desaturase gene

<400> SEQUENCE: 66
ttacttcttg aaaaagacca cgtctccctg atcctccacg                            40

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      Delta-6 forward primer

<400> SEQUENCE: 67
aatggctgct gctcccagtg tg                                               22

<210> SEQ ID NO 68
<211> LENGTH: 22
<212> TYPE: DNA
```

```
-continued

<213> ORGANISM: Artificial Sequence
<220> FEATURE:
<223> OTHER INFORMATION: Description of Artificial Sequence: Synthetic
      Delta-6 reverse primer

<400> SEQUENCE: 68
ttactgcgcc ttacccatct tg                                              22

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      Delta-12 forward primer

<400> SEQUENCE: 69
aatggcacct cccaacacta tc                                              22

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      Delta-12 reverse primer

<400> SEQUENCE: 70
ttacttcttg aaaaagacca c                                               21
```

PROCESS FOR PRODUCING POLY-UNSATURATED FATTY ACIDS BY OLEAGINOUS YEASTS

This Nonprovisional application claims priority under 35 U.S.C. §119(e) on U.S. Provisional Application No(s). 60/568,692 filed on May 7, 2004, the entire contents of which are hereby incorporated by reference.

BACKGROUND OF INVENTION

Commercial quantities of oils are mostly obtained from plants. Non-plant sources of oils are used commercially primarily because oils with different properties, determined by the fatty acids, are available. Oils are also accumulated by some yeasts and filamentous fungi. Of the some 600 different yeast species, only 25 or so are able to accumulate more than 20% lipid (Ratledge, *Biochem Soc Trans.* 1989;17: 1139-41), these are the oleaginous species.

Microbial lipids could contribute to the covering of the increasing demand of fats and oils. In addition, single cell oil (SCO) is of particular interest due to the capacity of oleaginous yeasts to convert numerous raw materials into value-added fats and oils.

Biosynthetic pathways of unsaturated fatty acid of mammalian physiological importance are depicted in FIG. 1. D12-desaturase, D6-desaturase and D15-desaturase, along with other enzymes involved in the conversion of fatty acids, e.g. those described in FIG. 1., are the enzymes of interest to introduce into oleaginous yeast.

Biosynthetic pathways of n-6 and n-3 polyunsaturated fatty acids of mammalian physiological importance are disclosed in FIG. 1. D12-desaturase is responsible for conversion of oleic acid (OA; 18:1, 6) to linoleic acid (LA; 18:2-9,12). D6-desaturase is responsible for conversion of LA to GLA (18:3-6, 9, 12) and of α-linolenic acid (ALA, 18:3-9, 12, 15) to stearidonic acid (SDA, 18:4-6, 9, 12, 15). These enzymes, along with other important enzymes involved in the conversion of fatty acids, e.g. those described in FIG. 1., are the enzymes of interest to introduce into oleaginous yeast.

The attractions of *Yarrowia lipolytica* as an oleaginous yeast with a capacity for growth on cheap carbon sources such as glucose led us to develop an unsaturated-fatty acid production system that can express exogenous genes involved in lipid biosynthesis.

DESCRIPTION OF PRIOR ART

Production of Gamma linoleic acid (GLA) by a D6-desaturase is described in U.S. Pat. No. 5,552,306. Production of 8, 11-eicosadienoic acid using *Mortierella alpine* is disclosed in U.S. Pat. No. 5,376,541. Production of docosahexaenoic acid by dinoflagellates is described in U.S. Pat. No. 5,407,957. Cloning of a D6-palmitoyl-acyl carrier protein desaturase is described in PCT publication WO 96/13591 and U.S. Pat. No. 5,614,400. Cloning of a D6-desaturase from borage is described in PCT publication WO 96/21022. Cloning of D9-desaturase is described in the published patent applications PCT WO 91/13972, EPO 550 162A1, EPO 561 569 A2, EPO 644 263A2, and EPO 736 598A1, and in U.S. Pat. No. 5,057,419. Cloning of D12-desaturases from various organisms is described in PCT publication WO 94/11516 and U.S. Pat. No. 5,443,974. Cloning of D15-desaturases from various organisms is described in PCT publication WO 93/11245. All publications and U.S. patents or applications referred to herein are hereby incorporated in their entirety by reference.

One of the limitations of using the metabolic pathway of oleaginous yeast to produce high value-added oils or fats is that those single or multiple enzymes required to convert the carbon source into the end product are lacking. It is long known in the art to produce oil not seen in the wild type by genetically introducing the necessary enzyme into transgenic plants. However, there has not been a successful attempt to achieve the same result in transgenic yeast.

BRIEF DESCRIPTION OF INVENTION

The invention is to provide A process of producing novel fatty acids in oleaginous yeast, comprising (1) producing oleaginous yeast by introducing the yeast with genes coding for enzymes selected from the group consisting of D5-desaturase, D6-desaturase, D12-desaturase, D15-desaturase and elongase; and (2) culturing the yeast in the medium containing high levels of carbon sources The invention is also to provide residues obtained from pressing oleaginous yeast produced by the process of the invention.

The invention is further to provide fatty acids generated from the process of the invention.

The invention is further to provide a composition comprising the fatty acid generated by the process of the invention.

BRIEF DESCRIPTION OF FIGURES

FIG. 1 discloses the biosynthetic pathway of n-6 and n-3 polyunsaturated fatty acids of mammalian physiological importance.

FIG. 2 discloses the cDNA sequence of *M. alpina* D6-desaturase (SEQ ID NO: 1).

FIG. 3 discloses the cDNA sequence of *M. alpina* D12-desaturase (SEQ ID NO: 2).

FIG. 4 DNA Primers used for the gene systhesis of *M. alpina* D6-desaturase (SEQ ID NO: 3-36).

FIG. 5 DNA Primers used for the gene systhesis of *M. alpina* D12-desaturase (SEQ ID NOS: 37-66).

DETAILED DESCRIPTION OF INVENTION

Figure 6:
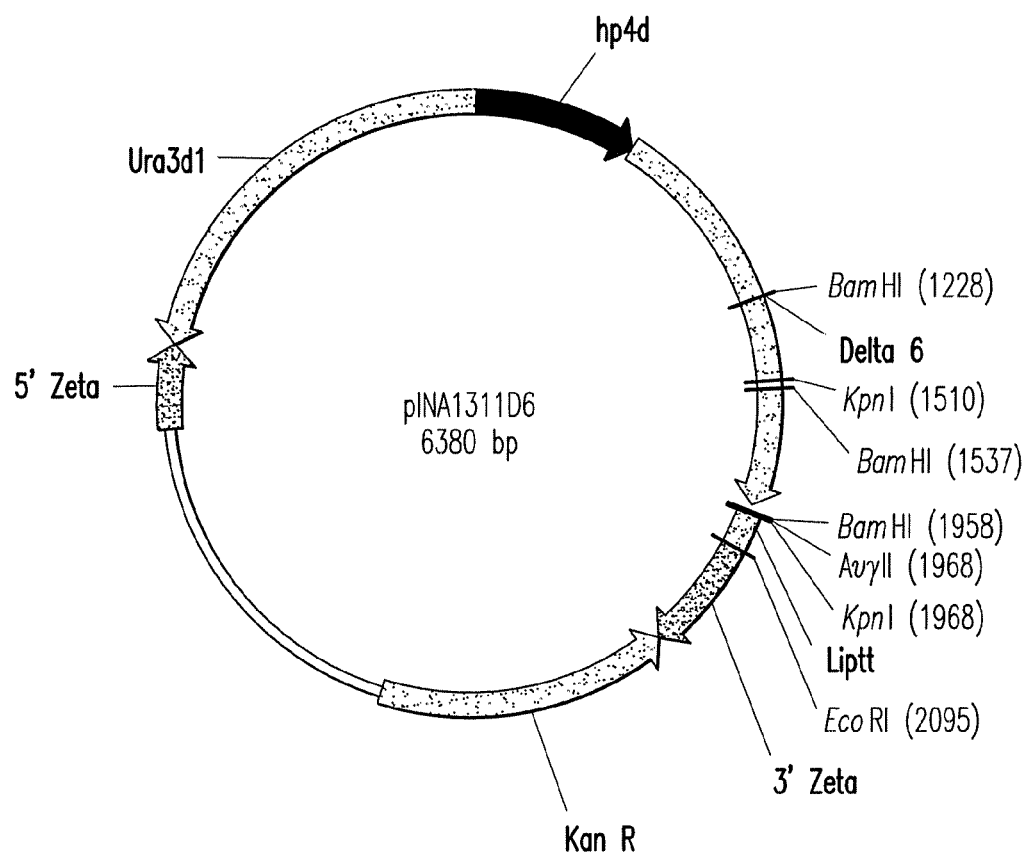
FIG. 6 discloses the construction map of pINA3111-D6.
Figure 7:
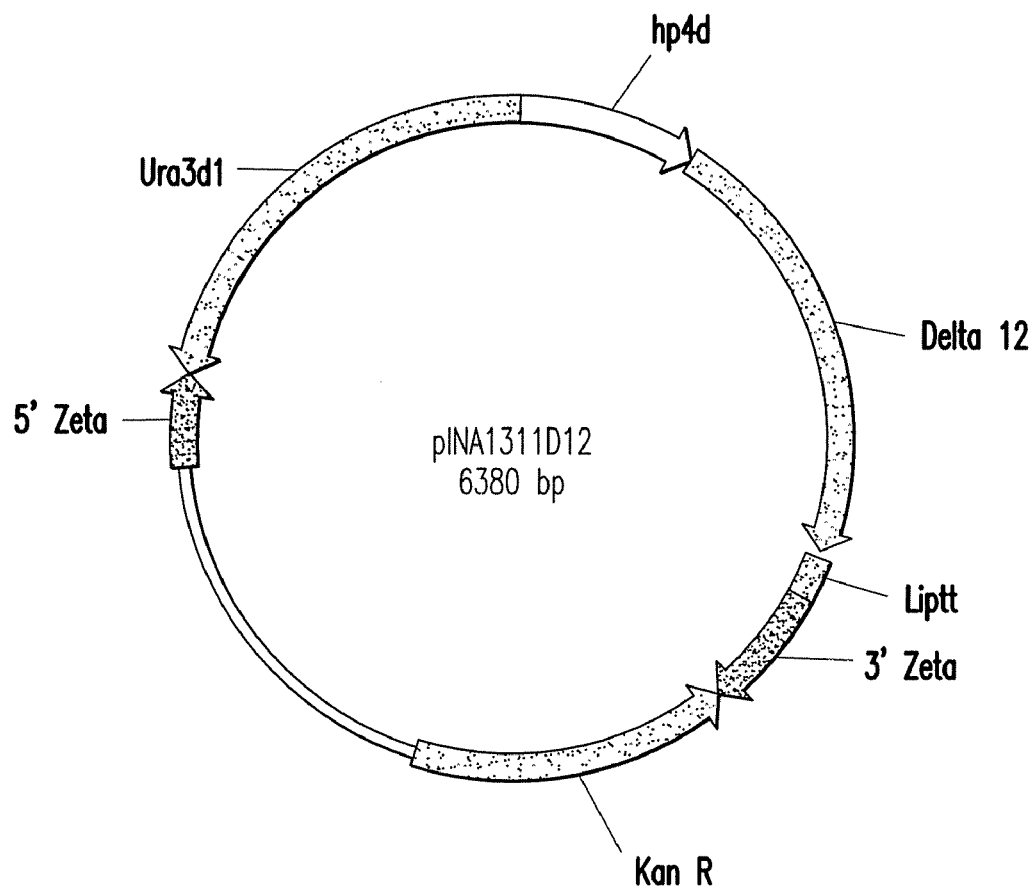
FIG. 7 discloses the construction map of pINA1311-D12.

The discovery that one strain of the oleaginous yeast has the capacity to grow on cheap carbon sources such as glucose led us to develop an unsaturated-fatty acid production system that can express exogenous genes involved in lipid biosynthesis.

The invention is to provide a process of producing novel fatty acids in oleaginous yeast, comprising (1) producing oleaginous yeast by introducing the yeast with genes coding for enzymes selected from the group consisting of D5-desaturase, D6-desaturase, D12-desaturase, D15-desaturase and elongase; and (2) culturing the yeast in the medium containing high levels of carbon sources.

The exogenous genes (such as those coding for enzymes selected from the group consisting of D5-desaturase, D6-desaturase, D12-desaturase, D15-desaturase and elongase) may be cloned or modified from other wild type strains of oleaginous yeast, or may not exist in oleaginous yeast at all.

The term "oleaginous yeast" used in the invention is directed to but is not limited to the yeast as follows:

Candida sp., Candida curvata D, Candida curvata R, Candida diddensiae, Cryptococcus (terricolus) albidus var. albidus, Cryptococcus laurentii, Endomycopsis vernalis, Hansenula ciferri, Hansenula saturnus, Lipomyces lipofer, Lipomyces starkeyi, Lipomyces tetrasporus, Rhodosporidium toruloides, Rhodotorula glutinis (gracilis), Rhodotorula graminis, Rhodotorula mucilaginosa, Trichosporon cutancum, Trichosporon pullulans, Trigonopsis variables, Yarrowia lipolytica, and Yarrowia paralipolytica.

In the process of the invention, the preferred oleaginous yeast is Yarrowia lipolytica.

According to the teaching of the examples, the oleaginous yeast used in the invention could express exogenous enzymes such as D6-desaturase, D5-desaturase, D12-desaturase, D15-desaturase and elongase. The preferred enzyme to be expressed in the oleaginous yeast is D6-desaturase and D12-desaturase. In the preferred embodiment of the invention, the D6-desaturase has the sequence as described in FIG. 2.

Introducing D12-desaturase into the oleaginous yeast can enhance the production of downstream metabolites (such as LA, ALA and GLA). The gene coding for D12-desaturase may be from oleaginous yeast or other organisms.

In the process of the invention, the carbohydrate source of the medium includes but is not limited to hexose, such as glucose, fructose, galactose, mannose, etc. The preferred hexose is glucose.

To test the oil production of oleaginous yeasts, several Yarrowia lipolytica strains were tested in several media. The strains under examination are ATCC8662, ATCC20226, ATCC48436 and polf (a gift from LGMC, INRA-CNRS, CBAI, INA P-G, Thiverval Grignon, France) It is found that in nutrition rich medium, e.g. YPD, Y. lipolytica grows faster but produces fewer oil (data not shown).

In nitrogen source-restricted medium, Y. lipolytica can produce large amounts of fat. Among all, yeasts in medium containing restricted nitrogen source, e.g. 1/50 YPD, grew the best. Medium YNB or the high salt medium suggested in Papanikolaou and Aggelis, 2002 were found to be unsuitable to support the production of fats (data not shown).

Therefore, we concluded that a small amount of YP (½~1/1000) and higher level of glucose in the medium are sufficient for Y. lipolytica to generate fat and at the same time require lower cost. Accordingly, in the process of the invention, the high level of carbon sources is defined as at least 3 times higher than the concentration of the nitrogen source.

From experiments above, the result of fat production of Y. lipolytica can be summarized as Table 1.

TABLE 1

Yeast growth, OA and LA production in different media.

|  | Growth | Fat production | Conversion efficiency of OA to LA |
|---|---|---|---|
| YL medium | ++ | ++ | +++ |
| YPD | ++++ | + | + |
| Diluted YPD | +++ | ++++ | ++ |
| YNB* | + | + | +++ |
| 9/10 YPD + 1/10 YL | +++ | ++ | ++ |

*YNB is medium using Yeast Nitrogen Base as nitrogen source.

Pressing the transgenic oleaginous yeast alone may not fully extract the high value-added oil generated by the process of the invention. Therefore, the residue of the pressed yeast, which contains some of the high-value-added oil, could have industrial applicability and may be used in feed, medicine, cosmetic or healthy food.

Therefore accordingly, the present invention is also to provide residues that are obtained from pressing oleaginous yeast produced by the process of the invention.

The present invention is further to provide fatty acids that are generated from the process of the invention. In particular, these fatty acids are selected from the group consisting of gamma-linolenic acid (GLA), alpha-linolenic acid (ALA), dihommo-gamma-linolenic acid (DGLA), arachidonic acid (AA), eicoatrienoic acid (EPA), adrenic acid, docosa-hexaenoic acid (DHA) and pinolenic acid. The preferred fatty acids generated by the process of the invention are GLA, ALA or pinolenic acid.

Additional oil selected from the group consisting of rice bran oil, sesame oil, fish oil, borage oil, evening primrose oil and black currant oil could be added to the composition of the invention for additional benefits.

EXAMPLES

Example 1

Cloning of D6-desaturase

The oleaginous yeast Y. lipolyitca was found to produce LA but not fatty acids downstream of the pathway shown in FIG. 1, such as GLA. The oleaginous yeast Y. lipolyitca is found in lack of D6-desaturase, which is the critical enzyme responsible for converting linoleic acid (LA) to GLA. Therefore we sought to generate transgenic Y. lipolyitca that produces GLA by introducing expression construct containing D6-desaturase cDNA sequence into Y. lipolyitca.

The cloning procedure was as follows:

Gene synthesis of M. alpina Delta 6 and Delta 12 desaturases

1. The cDNA sequence of M. alpina D6-desaturase was found in the GenBank database. The cDNA sequence of D6-desaturase is shown in FIG. 2.

2. Primer design: 60-mer as an unit, 20 bp as non-overlapped space between 2 units.

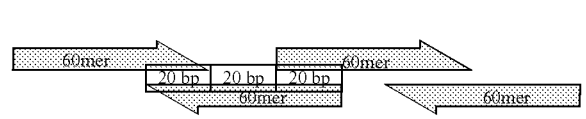

3. Mix all primers together, and perform the first PCR reaction. Using the first PCR product as template, perform the second PCR reaction as directed by the reference: Single-step assembly of a gene and entire plasmid from large numbers of oligodeoxyribonucleotides. Gene. 1995 16:49-53.

4. Clone and sequence the PCR products, select the right D6-desaturase and D12-desaturase genes for further study.

The above procedure was summarized as follows:

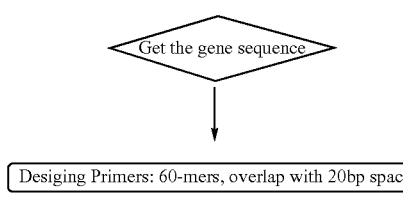

-continued

Example 2

Constructing Expression Vector pINA1311-D6 and pINA1311-D12

1. pINA1311 -D6 vector construction pINA1311 vector (a gift from LGMC, INRA-CNRS, CBAI, INA P-G, Thiverval Grignon, France, a vector system described in *FEMS Yeast research* 2: 371-379) digested with the restriction enzyme PmlI, in the 100 µl reaction buffer: 1X NE Buffer I, 1 mM $MgCl_2$, 20 µg pINC1311, 20U PmlI, 2U shrimp alkaline phosphatase (SAP), 37° C., 16 hr, using Gel extraction kits (Viogene) for recovering pINA1311.

Delta-6 desaturase gene was PCR amplified with D6F and D6R as primers, in the 50 µl reaction buffer: 20 mM Tris-HCl (pH 8.8 at 25° C.), 10 mM $(NH_4)_2SO_4$, 10 mM KCl, 0.1% Triton X-100, 0.1 mg/ml BSA, 20 mM $MgSO_4$, 0.4 µM primer, 0.2 mM dNTP, 2.5U Pfu DNA polymerase (MBI Fermentas),

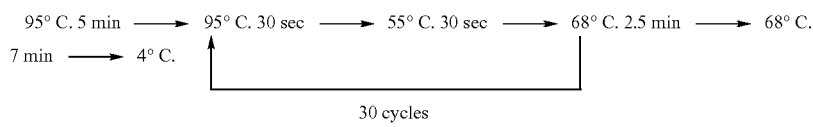

Purify the Delta-6 PCR product (Gel extraction kits), phosphorylate 5' end in the 100 µl reaction buffer: 1X T4 kinase buffer, 1 mM ATP, 40 µl PCR product, 12.5U T4 kinase, 37° C., 16 hr. Purify with Gel extraction kits.

In the ligation reaction, the ratio of pINA1311 : Delta-6 is 1:9, in a 10 µl ligation reaction buffer: 40 mM Tris-HCl, 10 mM $MgCl_2$, 10 mM DTT, 0.5 mM ATP, 5% PEG4000, 3U T4 DNA ligase, 22° C., 30min. Take 5 µl ligation product and mix with 100 µl competent cell, the transformation protocol is: 30 min ice-bath→45sec 42° C. heat shack→30 min ice-bath. Plate onto 20 ml LBKm (with 25 µg/ml kanamycin ) agarose plate. Perform colony PCR net day using D6R, 1311-SF as primer set. Identify the positive clones by sequencing.

2. pINA 1311 -D12 vector construction pINA1311 vector (a gift from LGMC, INRA-CNRS, CBAI, INA P-G, Thiverval Grignon, France, a vector system described in *FEMS Yeast research* 2: 371-379) is digested with the restriction enzyme PmlI, in the 100 µl reaction

TABLE 2 primers for vector construction.

| Primer name | Sequence | | Note |
|---|---|---|---|
| D6F | 5'-AATGGCTGCTGCTCCCAGTGTG-3' | (SEQ ID NO: 67) | Delta-6 forward primer |
| D6R | 5'-TTACTGCGCCTTACCCATCTTG-3' | (SEQ ID NO: 68) | Delta-6 reverse primer |
| D12F | 5'-AATGGCACCTCCCAACACTATC-3' | (SEQ ID NO: 69) | Delta-12 forward primer |
| D12F | 5'-TTACTTCTTGAAAAGACCAC-3' | (SEQ ID NO: 70) | Delta-12 reverse primer | buffer: 1X NEBuffer I, 1 mM MgCl$_2$, 20 μg pINC1311, 20U PmlI, 2U shrimp alkaline phosphatase (SAP), 37° C., 16 hr. Use Gel extraction kits (Viogene) for recovering pINA 1311.

Delta-12 desaturase gene is PCR amplified with D12F and D12R as primer, in the 50 μl reaction buffer: 20 mM Tris-HCl (pH 8.8 at 25° C.), 10 mM (NH$_4$)$_2$SO$_4$, 10 mM KCl, 0.1% Triton X-100, 0.1 mg/ml BSA, 20 mM MgSO$_4$, 0.4 μM primer, 0.2 mM dNTP, 2.5U Pfu DNA polymerase (MBI Fermentas),

| | |
|---|---|
| PEG 50% | 90 uL |
| LiOAc (2 M) | 5 uL |
| DTT (2 M) | 5 uL |
| SSDNA (10K) | 2.5 uL |
| R.E. digested (linearlized) vector | 5 μL |

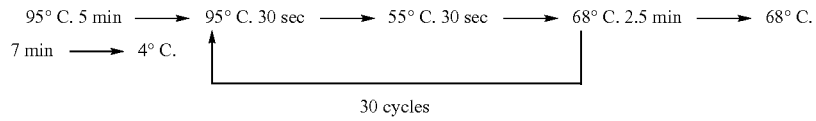

Purify the Delta-12 PCR product (Gel extraction kits), phosphorylate 5' end in the 100 μl reaction buffer: 1X T4 kinase buffer, 1 mM ATP, 40 μl PCR product, 12.5U T4 kinase, 37° C., 16 hr. Purify with Gel extraction kits.

In the ligation reaction, the ratio of pINA 1311: Delta-12 is 1:9, in a 10 μl ligationreaction buffer: 40 mM Tris-HCl, 10 mM MgCl$_2$, 10 mM DTT, 0.5 mM ATP, 5% PEG4000, 3U T4 DNA ligase, 22° C., 30 min. Take 5 μl ligation product and mix with 100 μl competent cell. The transformation protocol is: 30 min ice-bath→45sec 42° C. heat shack→30 min ice-bath. Plate onto 20 ml LBKm (with 25 μg/ml kanamycin) agarose plate. Perform colony PCR next day using D12R, 1311-SF as primer set. Identify the positive clones by sequencing with 1311-SF and 1311-SR primer.

Example 3

Transformation of *Y. lipolytica* Using Expression Vector pINA1311-D6 and pINA1311-D12

*Y. lipolytica* Transformation

| Materials and methods | |
|---|---|
| YNBD + CG plate (1 L) | One-step Transformation buffer |
| Yeast nitrogen base (w/o a.a and A.S.) 1.7 g | PEG 50% |
| Ammonium sulfate 5 g | 2 M LiOAc |
| casamino acid 1 g | 2 M DTT |
| sodium glutamate 1 g | SSDNA (10~12K) |
| glucose 2% | |
| agarose 2% | |
| a.a. | |

Transformation Protocol
1. Pick up several yeast (Polf) colonies. Dissolve in 1 ml ddH2O, vortex for seconds.
2. Check the cell density under microscope. Adjust the cell density to 1~5×10$^7$/ml.
3. Plate each YPD plate with 100 μl aliquot (1~5×10$^6$/plate). Incubate at 28° for 20~24 hours.
4. Digest the pINA1311D6 and pINA1311D12 with Not I R.E. Final concentration is 0.2 μg/μl.
5. Scrape cells from plate with tooth pick. Dissolve cells in 1 ml ddH2O. Calculate the cell density.
6. Spin down about 5×10$^7$ cells (3000 g, 5 min.). Discard the supernatant. Mix with the buffer:

7. Mix well by vortexing at 39° on water bath for 1 hour.
8. Plate onto YNBD+CG agar. Incubate at 28° or 30°.
9. Monocopy vector-transformed colonies will appear at the 2$^{nd}$-3$^{rd}$ days. The efficiency is about 10$^{3-4}$/microgram vector.

Example 4

Fat Production and Analysis of D6 Desaturase Activity

*Y. lipolytica* polf was transformed with vectors Pina1311-D6 to obtain transformed *Y. lipolytica* for D6 desaturase production.

Culture and Analysis of p1311-D6 and p1311 D12 transformants of Polf

1. Randomly pick up 6 transformants of pINA1311D6 and pINA1311D12. Culture and analyze 2 times.
2. Inoculate single colony of polf transformants of p1311-D6 & p1311-D12 in a 50-ml flask that contains 10 ml YPD at room temperature. Shake at 200 rpm, overnight.
3. Subculture 5×10$^7$~1×10$^8$ cells into a 50 ml modified YPD medium (1/50 YP+D in a 250 ml flask) at room temp. Shake at 200 rpm for 48 hours.
4. The analysis method: Lipids are extracted according to the protocol in Folch et al., *J Biol Chem* 226:497-509, 1957. Methylation of lipids are performed according to Morrison et al., *J Lipid Res* 5:600-608, 1964 or Metcalfe et al., *Anal Chem* 38:514-515, 1966. The GC analysis is performed following the protocol: the fatty acids were quantified using a gas chromatograph equipped with a flame-ionization detector and a fused-silica capillary column. The temperature of the injector and detector is 23° C. The fatty acid methyl ester was identified by comparing the retention time of sample peaks with peaks of commercial standards.

The results are summarized in the tables below:

TABLE 3 culture and analysis of pINA1311D6 transformants of polf.

| Sample No. | D6-1 | D6-2 | D6-3 | D6-4 | D6-5 | D6-6 |
|---|---|---|---|---|---|---|
| OA(Oleic acid, C18:1w9) in TG (%) | 48.13 | 46.80 | 47.66 | 45.30 | 48.96 | 47.44 |
| LA(Linoeic acid, C18:2w6) in TG (%) | 17.93 | 18.87 | 19.84 | 22.25 | 19.67 | 20.21 |

TABLE 3-continued culture and analysis of pINA1311D6 transformants of po1f.

| Sample No. | D6-1 | D6-2 | D6-3 | D6-4 | D6-5 | D6-6 |
|---|---|---|---|---|---|---|
| GLA(γ-linolenic acid, C18:3w6) in TG (%) | 1.71 | 1.77 | 0.29 | 0.24 | 0.26 | 0.29 |
| ☐D6 conversion rate (%) | 8.69 | 8.57 | 1.44 | 1.07 | 1.30 | 1.44 |
| OA in TG (%) | 48.13 | 46.80 | 47.66 | 45.30 | 48.96 | 47.44 |
| LA + GLA in TG (%) | 19.64 | 20.64 | 20.12 | 22.50 | 19.93 | 20.50 |
| OA + LA + GLA in TG (%) | 67.77 | 67.44 | 67.79 | 67.79 | 68.89 | 67.94 |
| ☐D12 conversion rate (%) | 28.98 | 30.60 | 29.69 | 33.18 | 28.93 | 30.18 |
| Average conversion (%) | | | 30.26 | | | |
| Standard error | | | 1.57 | | | |

TABLE 4 culture and analysis of pINA1311D6 transformants of po1f.

| Sample No. | D6-1 | D6-2 | D6-3 | D6-4 | D6-5 | D6-6 |
|---|---|---|---|---|---|---|
| OA(Oleic acid, C18:1w9) in TG (%) | 46.64 | 45.62 | 47.04 | 45.01 | 47.55 | 46.63 |
| LA(Linoeic acid, C18:2w6) in TG (%) | 18.89 | 19.82 | 20.47 | 22.54 | 21.11 | 21.09 |
| GLA(γ-linolenic acid, C18:3w6) in TG (%) | 1.78 | 1.82 | 0.27 | 0.23 | 0.28 | 0.27 |
| ☐D6 conversion rate (%) | 8.63 | 8.43 | 1.30 | 0.99 | 1.29 | 1.25 |
| OA in TG (%) | 46.64 | 45.62 | 47.04 | 45.01 | 47.55 | 46.63 |
| LA + GLA in TG (%) | 20.67 | 21.64 | 20.74 | 22.77 | 21.38 | 21.36 |
| OA + LA + GLA in TG (%) | 67.31 | 67.27 | 67.77 | 67.78 | 68.93 | 67.98 |
| ☐D12 conversion rate (%) | 30.71 | 32.18 | 30.60 | 33.59 | 31.02 | 31.42 |
| Average conversion (%) | | | 31.59 | | | |
| Standard error | | | 1.14 | | | |

TABLE 5 culture and analysis of pINA1311D12 transformants of po1f.

| Sample No. | D12-1 | D12-2 | D12-3 | D12-4 | D12-5 | D12-6 |
|---|---|---|---|---|---|---|
| OA(Oleic acid, C18:1w9) in TG (%) | 41.95 | 42.66 | 42.43 | 39.77 | 42.48 | 41.63 |
| LA(Linoeic acid, C18:2w6) in TG (%) | 27.33 | 25.45 | 25.58 | 29.13 | 27.37 | 26.89 |
| ☐D6 conversion rate (%) | | | Non detectable | | | |
| OA in TG (%) | 41.95 | 42.66 | 42.43 | 39.77 | 42.48 | 41.63 |
| LA + GLA in TG (%) | 27.33 | 25.45 | 25.58 | 29.13 | 27.37 | 26.89 |
| OA + LA + GLA in TG (%) | 69.28 | 68.10 | 68.01 | 68.89 | 69.85 | 68.52 |
| ☐D12 conversion rate (%) | 39.45 | 37.36 | 37.61 | 42.28 | 39.18 | 39.25 |
| Average conversion (%) | | | 39.19 | | | |
| Standard error | | | 1.76 | | | |

TABLE 6 culture and analysis of pINA1311D12 transformants of po1f.

| Sample No. | D12-1 | D12-2 | D12-3 | D12-4 | D12-5 | D12-6 |
|---|---|---|---|---|---|---|
| OA(Oleic acid, C18:1w9) in TG (%) | 44.42 | 43.91 | 45.15 | 42.93 | 43.87 | 43.51 |
| LA(Linoeic acid, C18:2w6) in TG (%) | 25.25 | 24.68 | 23.55 | 25.62 | 25.39 | 24.89 |
| ☐D6 conversion rate (%) | | | Non detectable | | | |
| OA in TG (%) | 44.42 | 43.91 | 45.15 | 42.93 | 43.87 | 43.51 |
| LA + GLA in TG (%) | 25.25 | 24.68 | 23.55 | 25.62 | 25.39 | 24.89 |
| OA + LA + GLA in TG (%) | 69.67 | 68.58 | 68.70 | 68.55 | 69.26 | 68.40 |
| ☐D12 conversion rate (%) | 36.25 | 35.98 | 34.28 | 37.37 | 36.66 | 36.39 |
| Average conversion (%) | | | 36.15 | | | |
| Standard error | | | 1.04 | | | |

It is shown that *Y. lipolytica* produced a large amount of fat in diluted YPD medium. After calculation, about 30~40% of the net weight of the extract yeast is fat. Of the fat, 65~75% is TG.

The D6-desaturase activity was measured as the conversion of LA into GLA. Comparing with the control, transformant D6-1 and D6-2 showed significant activity (about 8-9% of LA was converted to GLA) whereas controls showed only 1.0%~1.5% activity. There is a variation among the D6 transformants. The host strain po1f (data not shown) and its D12 transformants showed no detectable D6-desaturase activity.

The D12-desaturase activity was found to be increased in the D12-1~6 transformants (converting OA-->LA). While comparing with the control group D6-1~6, activities of D12-desaturase in all D12 transformants strains were increased. Among all strains, the activity of D12-desaturase in D12-4 increased the most. There is also a variation of D12 desaturase activity among the transformants.

To summarize the examples above, the inventions demonstrated a new strategy of improving the quantity and quality of oil produced by the transgenic yeast. The LA production increased comparing to its host control, and GLA can be produced by introducing exogenous D6 desaturase gene. Both findings indicate a new method that increases the oil pool and also produces new oil.

What is claimed is:

1. A process for producing gamma-linolenic acid (GLA) in oleaginous yeast capable of producing linolenic acid, comprising
   (1) producing oleaginous yeast by transforming the yeast with a gene encoding a D6-desaturase enzyme having a nucleic acid sequence as described in SEQ ID NO: 1, wherein the gene is integrated into a chromosome of the yeast and
   (2) culturing the yeast in a medium containing high levels of carbon sources, which are at least three times the concentration of a nitrogen source;
   wherein the expression of the genes is driven by a hp4d promoter.

2. The process according to claim 1, wherein the oleaginous yeast is selected from the group consisting of *Candida* sp., *Candida curvata D, Candida curvata R, Candida didensiae, Cryptococcus* (terricolus) *albidus var. albidus, Cryptococcus laurentii, Endomycopsis vernalis, Hansenula ciferri, Hansenula saturnus, Lipomyces lipofer, Lipomyces starkeyi, Lipomyces tetrasporus, Rhodosporidium toruloides, Rhodotorula glutinis* (gracilis), *Rhodotorula graminis, Rhodotorula mucilaginosa, Trichosporon cutancum, Trichosporon pullulans, Trigonopsis variables, Yarrowia lipolytica,* and *Yarrowia paralipolytica.*

3. The process according to claim 2, wherein the oleaginous yeast is *Yarrowia lipolytica.*

4. The process according to claim 1, wherein the carbon source is one or more hexose compounds or one or more disaccharide compounds.

5. The process according to claim 4, wherein the hexose is glucose, or the disaccharide is sucrose.

* * * * *